United States Patent
Richer et al.

(10) Patent No.: US 10,737,070 B2
(45) Date of Patent: Aug. 11, 2020

(54) APPARATUS AND METHOD FOR NAVIGATING A MEDICAL DEVICE

(71) Applicant: St. Jude Medical, Cardiology Division, Inc., St. Paul, MN (US)

(72) Inventors: Louis-Philippe Richer, Montreal (CA); Stuart Rosenberg, Castaic, CA (US); Jatin Relan, Talence (FR); Kyungmoo Ryu, Palmdale, CA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 149 days.

(21) Appl. No.: 15/730,121

(22) Filed: Oct. 11, 2017

(65) Prior Publication Data

US 2018/0099125 A1  Apr. 12, 2018

Related U.S. Application Data

(60) Provisional application No. 62/406,450, filed on Oct. 11, 2016.

(51) Int. Cl.
*A61M 25/09* (2006.01)
*A61B 34/20* (2016.01)
(Continued)

(52) U.S. Cl.
CPC ..... *A61M 25/09041* (2013.01); *A61B 5/0066* (2013.01); *A61B 5/0084* (2013.01);
(Continued)

(58) Field of Classification Search
CPC ........... A61B 2017/00725; A61B 2017/22038; A61B 2034/2055; A61B 2034/2059;
(Continued)

(56) References Cited

U.S. PATENT DOCUMENTS 5,437,290 A    8/1995    Bolger et al.
5,709,661 A *   1/1998    Van Egmond ..... A61B 1/00147
                                                     33/512

(Continued)

FOREIGN PATENT DOCUMENTS

EP           1574825 A1    9/2005
WO      2015061627 A1    4/2015

OTHER PUBLICATIONS

Reeves RR, Ang L, Bahadorani J, et al. Invasive cardiologists are exposed to greater left sided cranial radiation: the Brain study (Brain Radiation Exposure and Attenuation During Invasive Cardiology Procedues). J Am Coll Cardiol Intv. 2015;81197-1206.

(Continued)

*Primary Examiner* — Quynh-Nhu H. Vu
(74) *Attorney, Agent, or Firm* — Armstrong Teasdale LLP (57) ABSTRACT

The present disclosure provides apparatuses and methods for navigating a medical device into the body of a patient during an intracoronary or other medical procedure. In many embodiments, the present disclosure includes the use of a guidewire managing assembly that may be used in combination with a guidewire that includes a medical positioning system sensor. This guidewire managing assembly and sensor enabled guidewire are used in combination with a medical positioning system to determine the position of a medical device, such as a catheter or catheter sheath, and specifically the tip of the catheter or catheter sheath, that is threaded over the guidewire during a procedure. The present disclosure further relates to methods of tracking a medical device, such as a catheter tip, inside the body of a subject during a procedure.

9 Claims, 8 Drawing Sheets

(51) Int. Cl.
*A61B 5/107* (2006.01)
*A61B 5/00* (2006.01)
*A61B 5/06* (2006.01)
*A61N 1/05* (2006.01)
*A61M 25/10* (2013.01)
*A61B 17/00* (2006.01)
*A61B 17/22* (2006.01)
*A61M 25/01* (2006.01)
*A61B 90/00* (2016.01)
*A61M 25/00* (2006.01)

(52) U.S. Cl.
CPC .............. *A61B 5/062* (2013.01); *A61B 5/066* (2013.01); *A61B 5/068* (2013.01); *A61B 5/1076* (2013.01); *A61B 34/20* (2016.02); *A61B 5/0071* (2013.01); *A61B 5/0073* (2013.01); *A61B 2017/00725* (2013.01); *A61B 2017/22038* (2013.01); *A61B 2034/2055* (2016.02); *A61B 2034/2059* (2016.02); *A61B 2090/061* (2016.02); *A61B 2090/062* (2016.02); *A61B 2090/0811* (2016.02); *A61M 25/10* (2013.01); *A61M 2025/0008* (2013.01); *A61M 2025/0166* (2013.01); *A61M 2025/09116* (2013.01); *A61M 2025/09125* (2013.01); *A61M 2205/3306* (2013.01); *A61M 2205/3317* (2013.01); *A61M 2205/3523* (2013.01); *A61N 1/05* (2013.01)

(58) Field of Classification Search
CPC ........ A61B 2090/061; A61B 2090/062; A61B 2090/0811; A61B 34/20; A61B 5/0071; A61B 5/0073; A61M 2025/0166; A61M 2025/09116; A61M 2025/09125; A61M 2205/3306; A61M 2205/3317; A61M 2205/3523; A61M 25/01; A61M 25/09; A61M 25/09041; A61M 25/10; A61N 1/05

See application file for complete search history.

(56) References Cited

U.S. PATENT DOCUMENTS

| | | | |
|---|---|---|---|
| 8,372,021 B2* | 2/2013 | Lampropoulos | A61B 90/06 600/587 |
| 2003/0187369 A1* | 10/2003 | Lewis | A61B 5/1076 600/587 |
| 2006/0161045 A1 | 7/2006 | Merril et al. | |
| 2006/0276838 A1* | 12/2006 | Wensel | A61B 17/0057 606/213 |
| 2007/0250006 A1* | 10/2007 | Court | A61B 5/064 604/117 |
| 2008/0167542 A1* | 7/2008 | Lampropoulos | A61B 90/06 600/345 |
| 2008/0262473 A1 | 10/2008 | Kornblau et al. | |
| 2009/0062739 A1 | 3/2009 | Anderson | |
| 2011/0230758 A1 | 9/2011 | Eichler et al. | |
| 2012/0130230 A1 | 1/2012 | Eichler et al. | |
| 2013/0231678 A1* | 9/2013 | Wenderow | A61B 34/30 606/130 |
| 2014/0066899 A1* | 3/2014 | Blacker | A61M 25/0147 604/510 |
| 2014/0261453 A1 | 9/2014 | Carlson | |
| 2015/0119702 A1* | 4/2015 | Mulumudi | A61B 5/065 600/424 |
| 2015/0352323 A1 | 12/2015 | Klocke et al. | |
| 2016/0175058 A1* | 6/2016 | Wenderow | A61B 5/742 600/424 |

OTHER PUBLICATIONS

International Search Report and Written Opinion issued in International Patent Application No. PCT/US2017/056086, dated Dec. 22, 2017, 19 pages.

* cited by examiner

APPARATUS AND METHOD FOR NAVIGATING A MEDICAL DEVICE

CROSS-REFERENCE TO RELATED APPLICATIONS

This application claims the benefit of U.S. Provisional Patent Application No. 62/406,450 filed Oct. 11, 2016, the contents of which are hereby incorporated by reference herein in their entirety.

A. FIELD OF THE DISCLOSURE

The present disclosure relates generally to navigating medical devices including catheters and catheter sheaths. In particular, in many embodiments, the present disclosure relates to a guidewire managing assembly and related methods of use for navigating a catheter or catheter sheath through the vasculature towards a target organ, such as the heart, in the body of a subject while monitoring its position for improved safety and efficacy.

B. BACKGROUND

Interventional cardiology works with numerous types of guidewires, sheaths and catheters for providing cardiac assessment and therapy. For example, electrophysiology catheters are used in a variety of diagnostic, therapeutic, and/or mapping and ablative cardiology procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death. Balloon catheters are also widely used in interventional cardiology for numerous treatments.

Typically, a catheter or catheter sheath is deployed and manipulated through a patient's vasculature to the intended site, for example, a site within a patient's heart. In many cases, the catheter or catheter sheath is used in combination with a leading guidewire so as to allow easier and safer access to the intended site. The guidewire may first be introduced into the vasculature to the intended site and then the catheter threaded over the guidewire to the site. In order to improve the overall procedure and outcome, it is desirable for an operator to know the position and orientation of the catheter, and specifically the tip of the catheter, and then to visualize the guidewire as it is navigated within the body of the patient in order to minimize physical injury to the tissues surrounding the desired organ and ensure that the guidewire reaches its intended target. Some general methods for determining the position and orientation of medical devices using fluoropaque markers such as a metallic coil and/or an active impedance-sensing electrode are known in the art. Improving these known methods may provide improved reliability and patient outcomes.

BRIEF SUMMARY OF THE DISCLOSURE

The present disclosure generally relates to apparatuses and methods for navigating a medical device into the body of a patient during an intracoronary or other medical procedure. In many embodiments, the present disclosure includes the use of a guidewire managing assembly that may be used in combination with a guidewire that includes a medical positioning system sensor. This guidewire managing assembly and sensor enabled guidewire are used in combination with a medical positioning system to determine the position of a medical device, such as a catheter or catheter sheath, and specifically the tip of the catheter or catheter sheath, that is threaded over the guidewire during a procedure. The present disclosure further relates to methods of tracking a medical device, such as a catheter tip, inside the body of a subject during a procedure. The present disclosure further relates to using the guidewire managing assembly in combination with other technologies including optical coherence tomography and/or an advanced visualizer tool to generated three dimensional maps to navigate medical devices to a target location so a percutaneous coronary intervention may be completed on a subject. Other embodiments and descriptions of the present disclosure are set forth in detail below.

In one embodiment, the present disclosure is directed to a guidewire managing assembly for determining the location of a medical device in a subject during a procedure. The guidewire managing assembly comprises a means for attaching the guidewire managing assembly to an instrument, an entry port for a guidewire, a means for measuring one or more lengths of a guidewire or section thereof, a mechanism for locking the measuring means, a means for determining measured values and calculating distances, and a means for transmitting one or more values and distances to a separate component.

In another embodiment, the present disclosure is directed to a method of tracking a catheter tip inside the body of a subject. The method comprises: (i) zeroing a guidewire managing assembly using a medical positioning system sensor enabled guidewire; (ii) recording a length of the medical positioning system sensor enabled guidewire at which the guidewire is aligned with a tip of a catheter shaft; (iii) recording a total length of the medical positioning system sensor enabled guidewire; (iv) introducing the medical positioning system sensor enabled guidewire into a target vessel in the body of a patient and monitoring and recording its position and location during introduction to derive a vessel profile; (v) introducing the catheter shaft over the medical positioning system sensor enabled guidewire and into the target vessel; and (vi) estimating the location of the tip of the catheter shaft in the vessel using the guidewire managing assembly and the location of the medical positioning system sensor enabled guidewire.

In another embodiment, the present disclosure is directed to a system for determining the location of a catheter tip in a subject during a procedure. The system comprises a medical positioning system sensor enabled guidewire, a catheter handle attached to a catheter shaft, and a guidewire managing assembly attached to the catheter handle. The guidewire managing assembly comprises an entry port for the medical positioning system sensor enabled guidewire, a means for measuring one or more lengths of the medical positioning system sensor enabled guidewire or section thereof, a mechanism for locking the measuring means, a means for determining measured values and calculating distances, and a means for transmitting one or more values and distances to a separate component.

In yet another embodiment, an apparatus includes at least first and second medical devices, and a displacement tracking mechanism. In one embodiment, the first medical device is configured for traversing a portion of a human vasculature, and includes a sensor fixed at a known location along the first medical device. An example of such a known location is proximate the distal end of the first medical device. The second medical device is also configured for traversing the portion of the human vasculature along a substantially common path traversed by the first medical device, where the first and second medical devices are movable relative to one another along the portion of the human vasculature. An example of such relative movement is where the second medical device is an "over-the-wire" device that has a lumen to facilitate passage of the first medical device therethrough. The displacement tracking mechanism is fixed at a known location along the second medical device, and configured to track a distance of movement of the first medical device relative to the known location along the second medical device to identify a location of the second medical device based on the known location of the sensor along the first medical device and the distance of movement of the first medical device relative to the known location along the second medical device.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure provides medical devices for use in the human vasculature for known medical purposes, and additionally provides apparatuses and methods for tracking and navigating the medical devices to a desired target site. In many embodiments of the present disclosure, a guidewire managing assembly is used in combination with a guidewire having embedded therein or thereon, generally at the distal tip of the guidewire, at least one medical positioning sensor, such as a magnetic coil. The guidewire managing assembly uses the sensor enabled guidewire in combination with a medical positioning system, such as a magnetic tracking system, that can track the sensor on the guidewire so as to allow tracking and navigation of a medical device that is threaded over the guidewire, such as a fixed length catheter shaft, to an intended site within the vasculature of the subject. By using measured lengths of the sensor enabled guidewire, and/or measured lengths of a section of the sensor enabled guidewire, the guidewire managing apparatus can provide data to a medical positioning system to allow for calculations that can accurately estimate the position of a second medical device (a catheter shaft, for example) within the vasculature to allow an operator to accurately navigate that device to a desired site with an increased confidence level of its actual location. The disclosed embodiments may lead to more consistent and improved patient outcomes.

For purposes of this description, the present disclosure will be generally described in connection with a catheter in combination with the sensor enabled guidewire. It is contemplated, however, that the described features and methods of the present disclosure as described herein may be equally suitable for use with other medical devices, including sheaths (sensor enabled sheath), introducers (sensor enabled introducer), and the like as would be appreciated by one of ordinary skill in the art based on the disclosure herein. For example, the principles described herein can be used with any two or more medical devices that are moved relative to one another along a substantially common path, such as along a common portion of the human vasculature. For example, a guidewire may move relative to a catheter (or to multiple devices such as relative to both a catheter and an introducer), or a catheter may be moved relative to an introducer, etc. in these situations, inclusion of a magnetic or other position sensor(s) on any of the devices can facilitate tracking of one or more of the other devices moving along a substantially common path, by tracking the relative distances between the sensor(s) on one device and a known point on one or more of the other devices. For purposes of facilitating an understanding of aspects of the disclosure, various embodiments are described herein in terms of a magnetic sensor(s) positioned at a known point on a guidewire, and the relative distance between that sensor and a known point on a catheter is tracked to enable identification of the position of the catheter. However, as noted above, the principles described herein may be employed between any number of medical devices, including guidewires, catheters, introducers, leads, and other medical devices or combinations thereof.

In many embodiments of the present disclosure, the guidewire managing assembly that uses the sensor enabled guidewire is used to specifically track the tip of a catheter within the vasculature of a subject undergoing an intracoronary procedure (such as placing a balloon catheter). By knowing the positioning of the tip of the catheter, the operator of the system can more effectively provide the desired therapy to the subject during the procedure. Additionally, with many of the embodiments described herein, the guidewire is able to retain its primary function of leading the catheter such that the catheter may be advanced or threaded over the guidewire to a desired location within the body of the patient. In other embodiments, the guidewire managing assembly may be used to assist in the positioning of one or more leads for cardiac rhythm management.

The guidewire managing assemblies of the present disclosure utilize a guidewire including at least one medical positioning sensor and work in combination with a medical positioning system and the various components thereof that can track the medical positioning sensor on a readable display for an operator to view in real time. One suitable medical positioning system for use in combination with the guidewire managing assemblies and the sensor enabled guidewires of the present disclosure is a MediGuide™ system (St. Jude Medical, Minneapolis, Minn.), which is one example of a visualization and navigation system that can display the position and orientation of devices including a MediGuide™ sensor on both live and prerecorded fluoroscopy in real time. The MediGuide™ sensor is located in three dimensional space using a low powered electromagnetic field. The suitable sensor, such as a metallic coil and/or an active impedance-sensing or impedance-sending electrode, may be embedded therein or thereon the guidewire to produce the sensor enabled guidewire. In some embodiments described herein, the MediGuide™ system may be used in combination with an EnSite™ Velocity™ cardiac mapping system including an advance visualizer tool (St. Jude Medical, Minneapolis, Minn.) to further the desired navigation.

Generally, the guidewire managing assemblies of the present disclosure will include a means for attaching the guidewire managing assembly to an instrument (in many embodiments a catheter handle), an entry port for a guidewire, a means for measuring one or more lengths of a guidewire or section thereof, a mechanism for locking the measuring means (if the measuring means is mechanical in nature as opposed to optical in nature), a means for determining measured values and calculating distances, and a means for transmitting one or more values and distances to a separate component, such as a medical positioning system. The guidewire managing assemblies and their uses are described in further detail hereinbelow.

Figure 1:
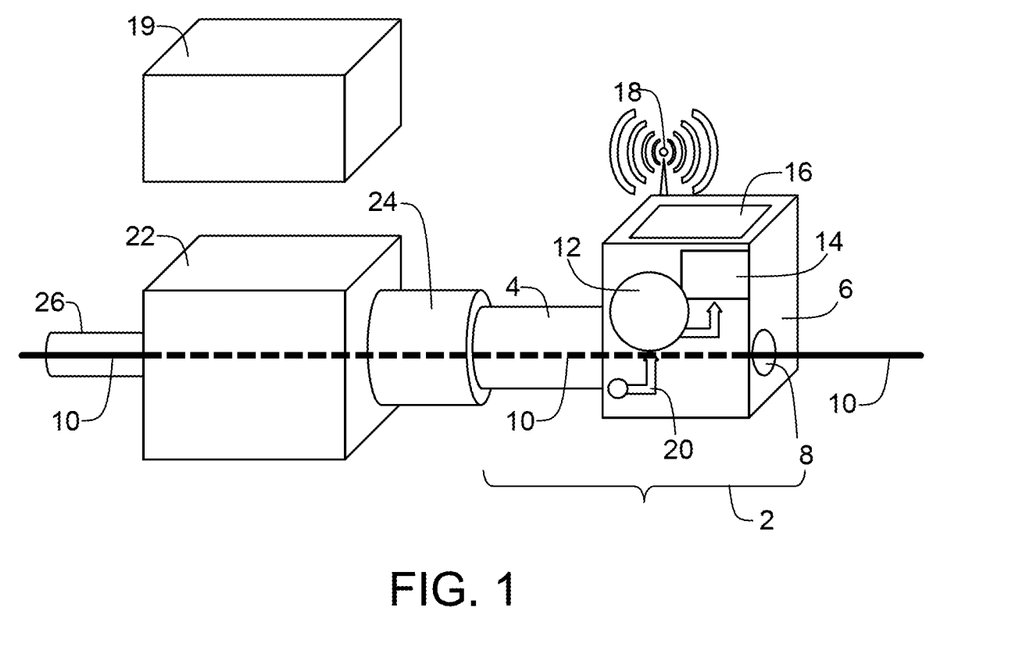
FIGS. 1 and 1A illustrate guidewire managing assemblies in accordance with embodiments of the present disclosure.

Referring now to the drawings, and specifically to FIG. 1, there is shown one embodiment of a guidewire managing assembly of the present disclosure. Guidewire managing assembly 2 includes an attachment or interface device, such as luer-lock tip 4 attached to body 6. Luer-lock tip 4 (or another suitable interface device or attachment mechanism) allows for guidewire managing assembly 2 to be attached to another device. Body 6 includes entry port 8 for allowing sensor enabled guidewire 10 (sensor not shown on guidewire) to enter body 6. Body 6 further includes measurement wheel 12 for measuring one or more lengths of sensor enabled guidewire 10, wheel locking mechanism 20 for locking measurement wheel 12, preventing wheel rotation in the absence of sensor enabled guidewire 10, and assisting in aligning the tip of sensor enabled guidewire 10 as described herein, circuit 14 (such as that provided by a circuit board or the like) for computing one or more values using data received from measurement wheel 12, and display screen 16 for optionally displaying one or more values as received from circuit 14. Also attached to circuit 14 on body 6 is wireless transmission antenna 18 for transmitting data wirelessly to another component 19, such as a medical positioning system, or component thereof. A wired connection could alternatively be used.

Referring again to FIG. 1, guidewire managing assembly 2 is attached to catheter handle 22 via luer-lock port 24 being attached to luer-lock tip 4. As illustrated in FIG. 1, sensor enabled guidewire 10 enters guidewire managing assembly 2 at entry port 8 and travels through luer-lock tip 4, luer-lock port 24, catheter handle 22, and into and out of catheter shaft 26.

The sensor utilized in combination with sensor enabled guidewire 10 may optionally include a housing applied over the sensor component which may be in the form of an adhesive, plastic tube, elastomeric tube by applying heat, and the like. In one specific embodiment, the sensor is in the form of an electromagnetic coil (i.e., a wound wire), which produces an electrical output in response to an electromagnetic field. The housing may be constructed of a metal, such as stainless steel, or the like. The sensor may be coupled to the guidewire by methods known in the art including welding, brazing, employing an adhesive, pressure fit, and the like. One or more than one sensor may be utilized on the guidewire for suitable navigation thereof.

Figure 1A:
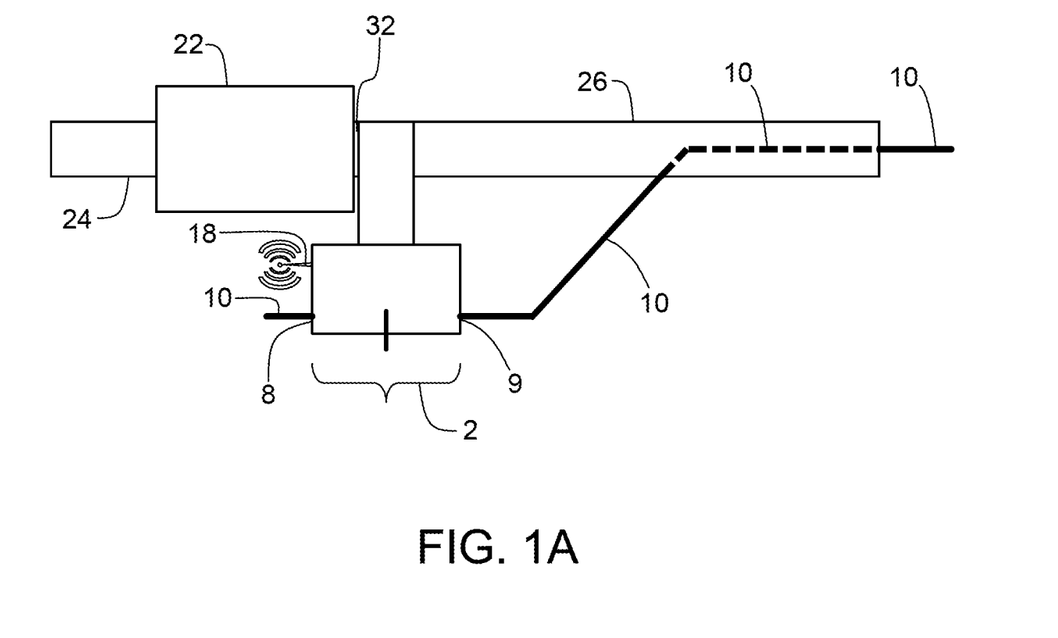

Referring now to FIG. 1A, an alternative embodiment is shown for using guidewire managing assembly 2 in combination with a monorail or rapid-exchange type of catheter. In this embodiment, guidewire managing assembly 2 is snapped to or otherwise affixed at a junction 32 between catheter shaft 26 and catheter handle 22. In this embodiment, luer-lock port 24 on catheter handle 22 may be utilized for another purpose as it is not attached to guidewire managing assembly 2. Sensor enabled guidewire 10 enters guidewire managing assembly 2 at entry port 8, exits at exit point 9, and is fed through catheter shaft 26 as described above.

Figure 2:
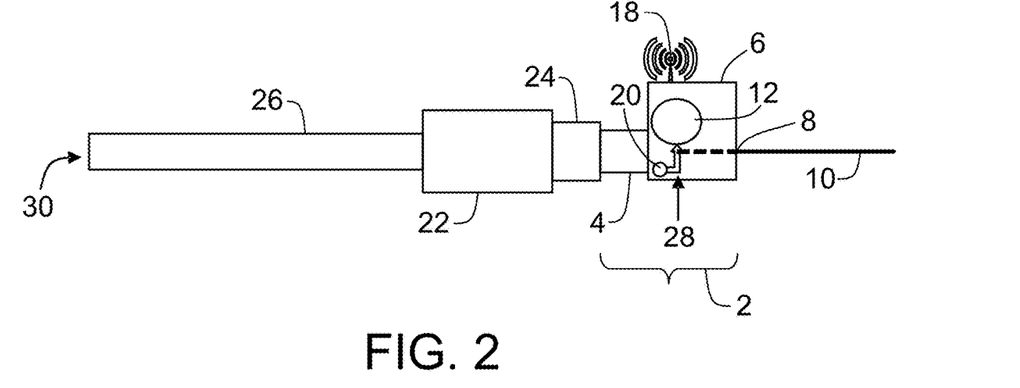
FIGS. 2, 3, and 4 illustrate various uses of a guidewire managing assembly of the present disclosure.
Figure 3:
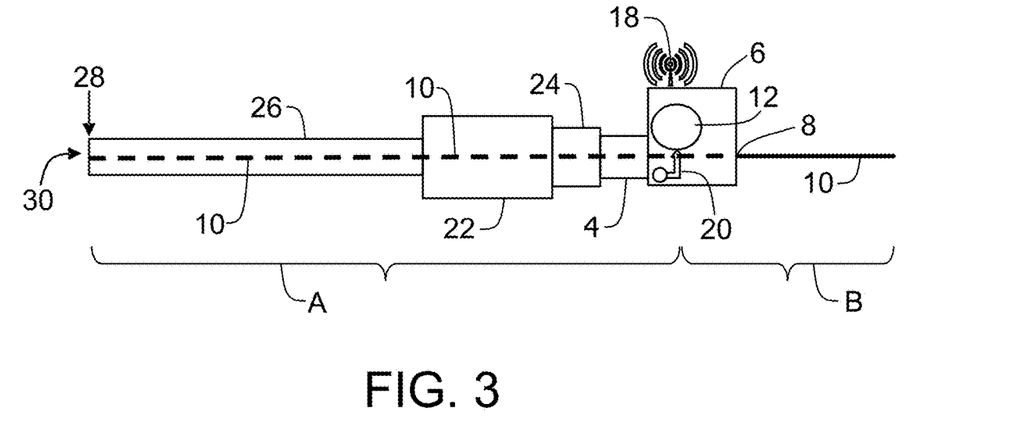

The guidewire managing assemblies of the present disclosure are used in combination with a sensor enabled guidewire (and a medical positioning system) as described herein to navigate and track a medical device advanced over the guidewire, such as a catheter, and specifically the tip of a catheter shaft. In use, the guidewire managing assembly is first "zeroed" or "tared" using the sensor enabled guidewire to prepare the guidewire managing assembly for use. Referring now to FIGS. 2 and 3, sensor enabled guidewire 10 is introduced into entry port 8 of body 6 of guidewire managing assembly 2 and the tip 28 of sensor enabled guidewire 10 is first aligned with measurement wheel 12, which will de-activate wheel locking mechanism 20, as shown in FIG. 2. Once tip 28 of sensor enabled guidewire 10 is aligned with measurement wheel 12, sensor enabled guidewire 10 is introduced through luer-lock tip 4 and luer-lock port 24, through catheter handle 22, and into catheter shaft 26. Tip 28 is aligned with distal end 30 of catheter shaft 26. Once tip 28 is aligned with distal end 30, the measurement by measurement wheel 12 is recorded by circuit 14 (not shown in FIGS. 2 and 3); this measurement is equal to the length of sensor enabled guidewire 10 required for tip 28 of sensor enabled guidewire 10 to be aligned with distal end 30 of catheter shaft 26. As shown in FIG. 3, this distance is equal to distance A.

Figure 4:
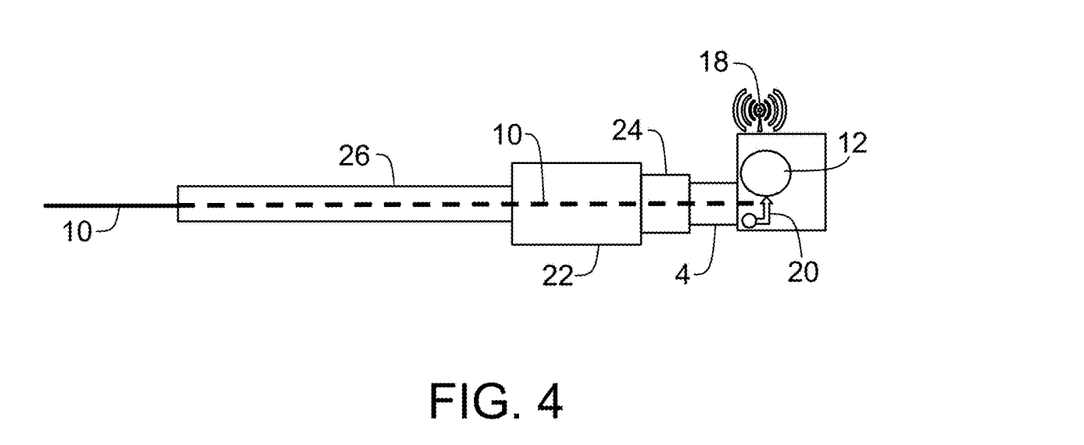

Once distance A (See FIG. 3) for sensor enabled guidewire 10 has been determined as described above, as further illustrated in FIG. 4 the entire length of sensor enabled guidewire 10 is threaded through measurement wheel 12 until the point at which wheel locking mechanism 20 locks measurement wheel 12 as the entire length of sensor enabled guidewire 10 has passed therethrough. Once wheel locking mechanism 20 locks measurement wheel 12, the distance is recorded by circuit 14 (not shown in FIG. 4 but illustrated in FIG. 1). This distance is equal to distance B as shown in FIG. 3. Once distances A and B (See FIG. 3) have been measured and recorded by guidewire management assembly 2, the entire length of sensor enabled guidewire 10, equal to distance A plus distance B, can be calculated, stored, and optionally transmitted wirelessly by wireless transmission antenna 18 to one or more other components or processors, such as components or processors of a medical positioning system (not shown in FIG. 4). These distances A and B may then be utilized by a medical positioning system to help navigate and track another medical device advanced over sensor enabled guidewire 10 as further described herein.

In some embodiments of the present disclosure, distance A plus distance B (that is, the entire length of the sensor enabled guidewire) may be manually input into the guidewire managing apparatus and/or the medical positioning system using the manufacturer's specifications for the sensor enabled guidewire. Also, in some embodiments, distance A may also be manually entered by using the specification from the sensor enabled guidewire, as well as the known length of the catheter shaft, catheter body, luer-lock port, luer-lock tip and the distance from the wheel locking mechanism to the body. Distance B can then be easily computed. If the distances for distance A and distance B are manually input into the medical positioning system based on product specifications, the "zeroing" or "taring" steps described above for determining distances A and B may not be required, although they could still be performed in some embodiments to confirm the specifications.

Figure 5:
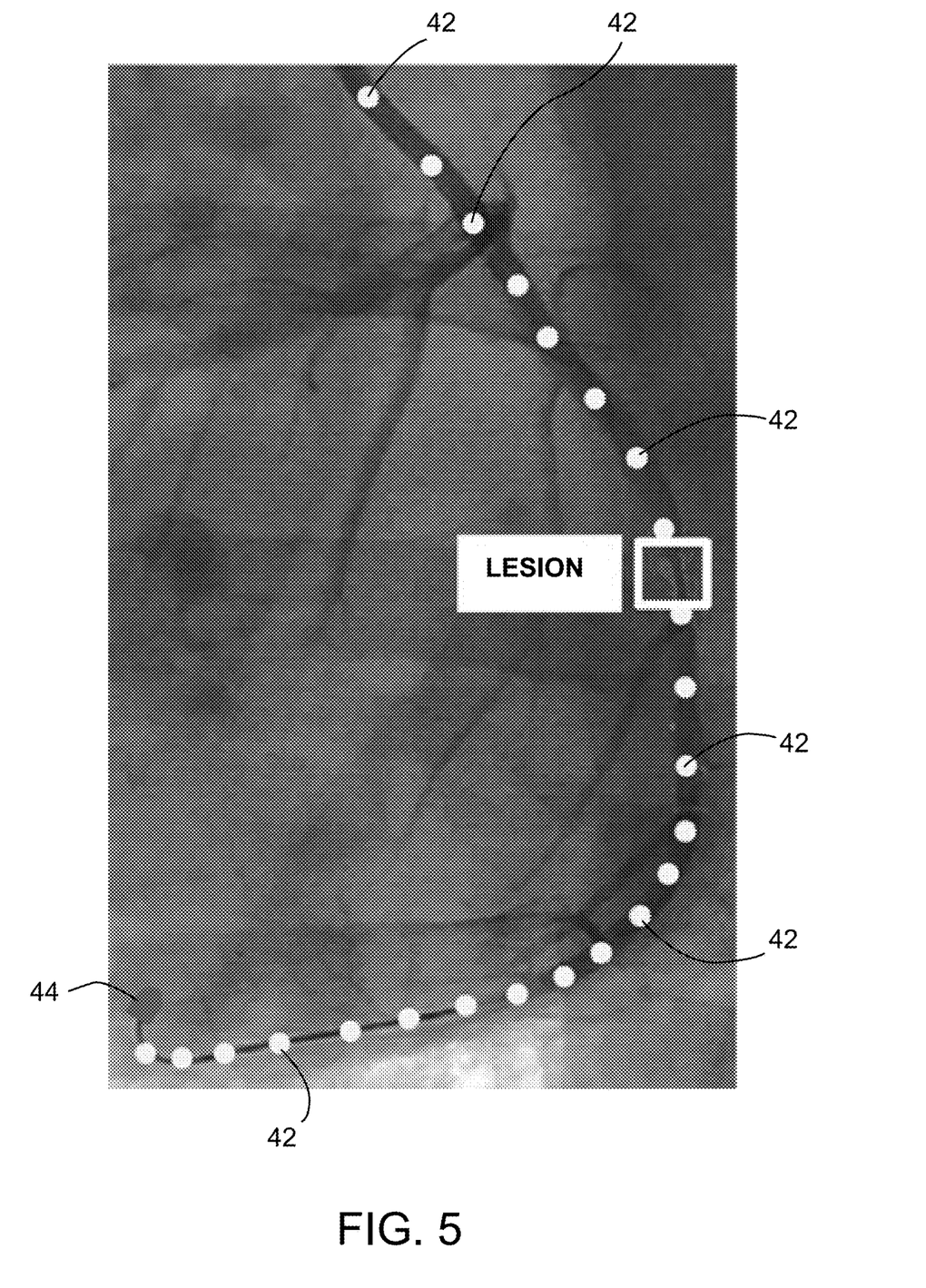
FIG. 5 is a photograph from a display showing the tracking pattern of a sensor enabled guidewire in a vessel.

Once distances A and B have been determined and input into a medical positioning system and the calibration is complete, the sensor enabled guidewire is removed from the guidewire managing assembly, catheter handle, and catheter shaft. Once removed, the sensor enabled guidewire may then be introduced into the vasculature of a subject by the operator, who may use a pre-recorded cine loop from the medical positioning system for guidance in and through the vasculature. In one embodiment, when the subject is undergoing a coronary procedure, the sensor enabled guidewire is introduced and guided into the coronary arterial network and threaded to the target site which may be, for example, a lesion. During this introduction into the coronary arterial network, the position and orientation of the sensor enabled guidewire is continuously monitored, tracked, and recorded using the medical positioning system and shown on a display, as illustrated in FIG. 5. FIG. 5 shows the continuous path (white dots 42) produced by the sensor on the sensor enabled guidewire (the tip of which is also shown in FIG. 5 as the head 44 at the end of white dots 42) as the sensor enabled guidewire is threaded through the vessel. This tracking pattern for the sensor enabled guidewire shown in FIG. 5 is the basis for a vessel profile described below.

Figure 6:
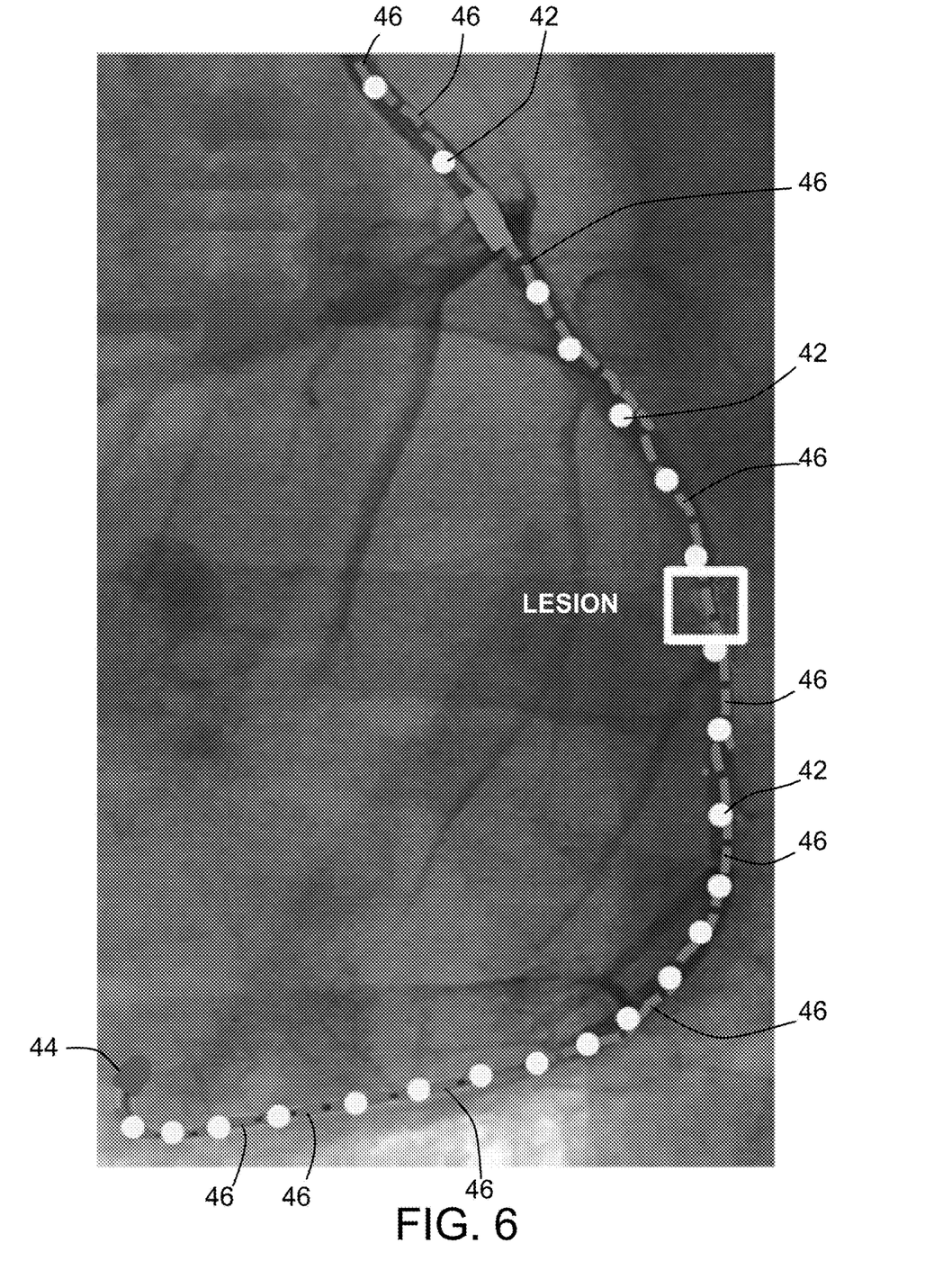
FIG. 6 is a photograph from a display showing a vessel profile created using a sensor enabled guidewire.

The continuous monitoring and tracking of the sensor enabled guidewire during the threading to the target site (and hence the tracking pattern shown in FIG. 5) allows the medical positioning system to derive a vessel profile or path of the vessel that can also be displayed by the medical positioning system as shown in FIG. 6 where the medical positioning system has generated line 46 for the path through the vessel. In many embodiments, the sensor enabled guidewire is threaded distal to the target point, such as a lesion (i.e., a narrowing of coronary artery), for example, to allow the vessel profile to extend past the target point for greater accuracy. In some embodiments, the vessel profile or path may be elucidated using by isolating the edges of the vessel, using, for example, a vessel edge detection algorithm commonly used with optical coherence tomography.

Once the medical positioning system has computed and displayed the vessel profile created using the sensor enabled guidewire and the target site (e.g., lesion) has been identified, the sensor enabled guidewire is left in place (with its entire progression saved in the medical positioning system thus resulting in a three dimensional vessel profile or path assessment as noted above) and the catheter shaft is threaded over the sensor enabled guidewire. As the catheter shaft is threaded and advanced over the sensor enabled guidewire and into the coronary arterial network, the leading sensor enabled guidewire is re-introduced into the guidewire managing assembly and contacts the measurement wheel, thereby releasing or de-activating the locking mechanism holding the measurement wheel in place allowing it to again track movement of the sensor enabled guidewire. As the sensor enabled guidewire comes back through the guidewire managing assembly and contacts the measurement wheel (as the catheter shaft is advanced further into the subject) the value of distance A plus distance B will decrease and these decreasing values may be continuously transmitted (optionally wirelessly) to the medical positioning system. When the sensor enabled guidewire or the catheter shaft are moved forward and backward during the procedure (individually and not both simultaneously) the measurement wheel is moved as well and the displacement can be quantified and recorded and/or transmitted to the processing unit of the medical positioning system. Because the catheter shaft has a known length from tip to proximal and the catheter body is of known length (i.e., a non-telescoping catheter body) the linear path/distance between the guidewire managing assembly and the catheter tip is constant, even with the catheter body bending or rotating to reach the target site. As such, the medical positioning system can calculate and compute (using the location of the sensor on the sensor enabled guidewire, the path followed by the catheter shaft when advancing over the sensor enabled guidewire (given by the vessel profile) and the distance between the sensor enabled guidewire and catheter shaft tip) an estimated position of the tip of the catheter shaft (as well as other common catheter features like the balloon position based on a specification sheet) and display it on the medical positioning system display screen relative to the sensor enabled guidewire in the generated vessel profile. This allows the operator of the system to see the estimated position of the tip of the catheter shaft relative to the lesion on the display and properly position the tip of the catheter so as to deliver the desired therapy in the correct location.

When the medical positioning system display indicates that the tip of the catheter is in the desired position adjacent the lesion, in some embodiments the estimated position of the catheter tip may be further confirmed if desired by keeping the catheter tip in place and threading the sensor enabled guidewire back to the catheter tip and confirming that the value displayed for distance A on the medical positioning system as described above matches the measured distance of distance A previously determined prior to insertion of the sensor enabled guidewire into the subject.

In an alternative embodiment of the present disclosure, the measurement wheel as described above for tracking the relative distance of the sensor enabled guidewire to the tip of the catheter shaft and measuring the total length of the sensor enabled guidewire may be replaced in the guidewire managing assembly with one or more optical devices and/or optical detectors used to track the displacement. In these embodiments, the locking mechanism may also optionally be removed from the guidewire managing assembly as well. In one alternative embodiment, at least one light emitting diode and two photodetectors may be located within the guidewire managing assembly attached to the proximal portion of the catheter handle. The photodetectors may have small windows approximately the same size of one filar of the sensor enabled guidewire, such that light reflected from the transmitting light emitting diode and collected by the photodetectors will depend primarily on whether the metal filar (high intensity) or the space between filars (low intensity) of the sensor enabled guidewire (generally helically wound) is in proximity to the detector window. Having a lookup table of standard pitch length specifications for common sensor-enabled guidewires, displacement of the sensor enabled guidewire may be determined by counting the peaks on a detector and multiplying this number by the pitch distance. The two photodetectors may be oriented approximately perpendicular to the axis of the sensor enabled guidewire such that during advancement of the sensor enabled guidewire (or retraction of the catheter shaft), one of the detectors will see a peak first, while during retraction of the sensor enabled guidewire (or advancement of the catheter shaft), the other detector sees the peak first. In this manner, both distance and sign are determined, using a simple system with a high temporal resolution.

In a further optical alternative embodiment an image capture device such as a charge coupled device (CCD) or the like may be used in place of the measurement wheel. These devices can record a strip or two dimensional array of optical image data, thus being able to visualize a portion of the sensor enabled guidewire itself rather than counting filars. An edge detection algorithm run on the resulting images can be used to track both the distance and the direction that the sensor enabled guidewire is moving relative to the sensor. In some embodiments, this optimal method may be desirable, especially when blood may be present on the sensor enabled guidewire.

Other embodiments of the present disclosure include methods of using the guidewire managing assembly as well kits or systems including the guidewire managing assembly. In one embodiment, a method of tracking a catheter tip inside the body of a subject is disclosed. The method comprises: (i) zeroing a guidewire managing assembly using a medical positioning system sensor enabled guidewire; (ii) recording a length of the medical positioning system sensor enabled guidewire at which the guidewire is aligned with a tip of a catheter shaft; (iii) recording a total length of the medical positioning system sensor enabled guidewire; (iv) introducing the medical positioning system sensor enabled guidewire into a target vessel in the body of a patient and monitoring and recording its position and location during introduction to derive a vessel profile; (v) introducing the catheter shaft over the medical positioning system sensor enabled guidewire and into the target vessel; and (vi) estimating the location of the tip of the catheter shaft in the vessel using the guidewire managing assembly and the location of the medical positioning system sensor enabled guidewire.

In another embodiment of the present disclosure, a system for determining the location of a catheter tip during a procedure utilizing the guidewire managing apparatus is disclosed. The system may include a medical positioning system sensor enabled guidewire, a catheter handle attached to a catheter shaft, and a guidewire managing assembly attached to the catheter handle. The guidewire managing assembly comprises an entry port for the medical positioning system sensor enabled guidewire, a means for measuring one or more lengths of the medical positioning system sensor enabled guidewire or section thereof, a mechanism for locking the measuring means, a means for determining measured values and calculating distances, and a means for transmitting one or more values and distances to a separate component.

In a further alternative embodiment of the present disclosure, the sensor enabled guidewire described herein may be used in combination with a conventional catheter and catheter shaft and/or a conventional introducer to monitor, track, and record the position of the tip of the catheter. In this embodiment, the sensor enabled guidewire is locked in position within the lumen of the catheter, or locked into position on the introducer, such that it is fixed in one place and cannot move absent movement of the catheter or introducer. By locking the sensor enabled guidewire to the catheter or introducer such that the tip of the sensor enabled guidewire and the tip of the catheter or introducer are aligned, the position and orientation tracking of the sensor enabled guidewire during advancement in the body of the subject would reveal the position and orientation of the catheter or introducer tip. In this embodiment, a vessel profile may be created as described above and the location of the catheter tip or introducer tip will be the same as the position of the tip of the sensor enabled guidewire.

In a further alternative embodiment of the present disclosure, the medical positioning system sensor may be located on an introducer to provide a sensor enabled introducer such that the tip of the introducer (where the sensor is located) may be monitored, tracked, and recorded as described herein. In one embodiment, the sensor enabled introducer may be used in combination with a Cardiac Resynchronization Therapy (CRT) lead and the position and placement of the CRT lead determined using the sensor enabled introducer.

In another embodiment of the present disclosure intracoronary navigation with near-zero fluoroscopy is disclosed using a combination of steps and methods, including the guidewire managing apparatus described herein. In one specific embodiment, near-zero fluoroscopy intracoronary navigation and balloon catheter (stent) expansion near a lesion may be obtained by using a combination of: (1) vessel profile creation and spatial location using the guidewire managing assembly described above in combination with a medical positioning system (such as the MediGuide™ "MDG" described above); (2) an optical coherence tomography (OCT) scan and percutaneous coronary intervention (PCI) planning; and (3) importing the vessel profile and special location data and OCT geometries in an advanced visualizer software (such as EnSite Velocity™ Platform; St. Jude Medical, Minneapolis, Minn.) and executing the planned PCI procedure. This combination of an advanced visualizer software, medical positioning system data, and an OCT scan allows an operator to acquire precise images for diagnostic and stent (or other device) planning, translate this planning in a 3D geometry imported into the advanced visualizer, and visualize the catheter tip and navigate in the 3D geometry for exact deployment.

Figure 7:
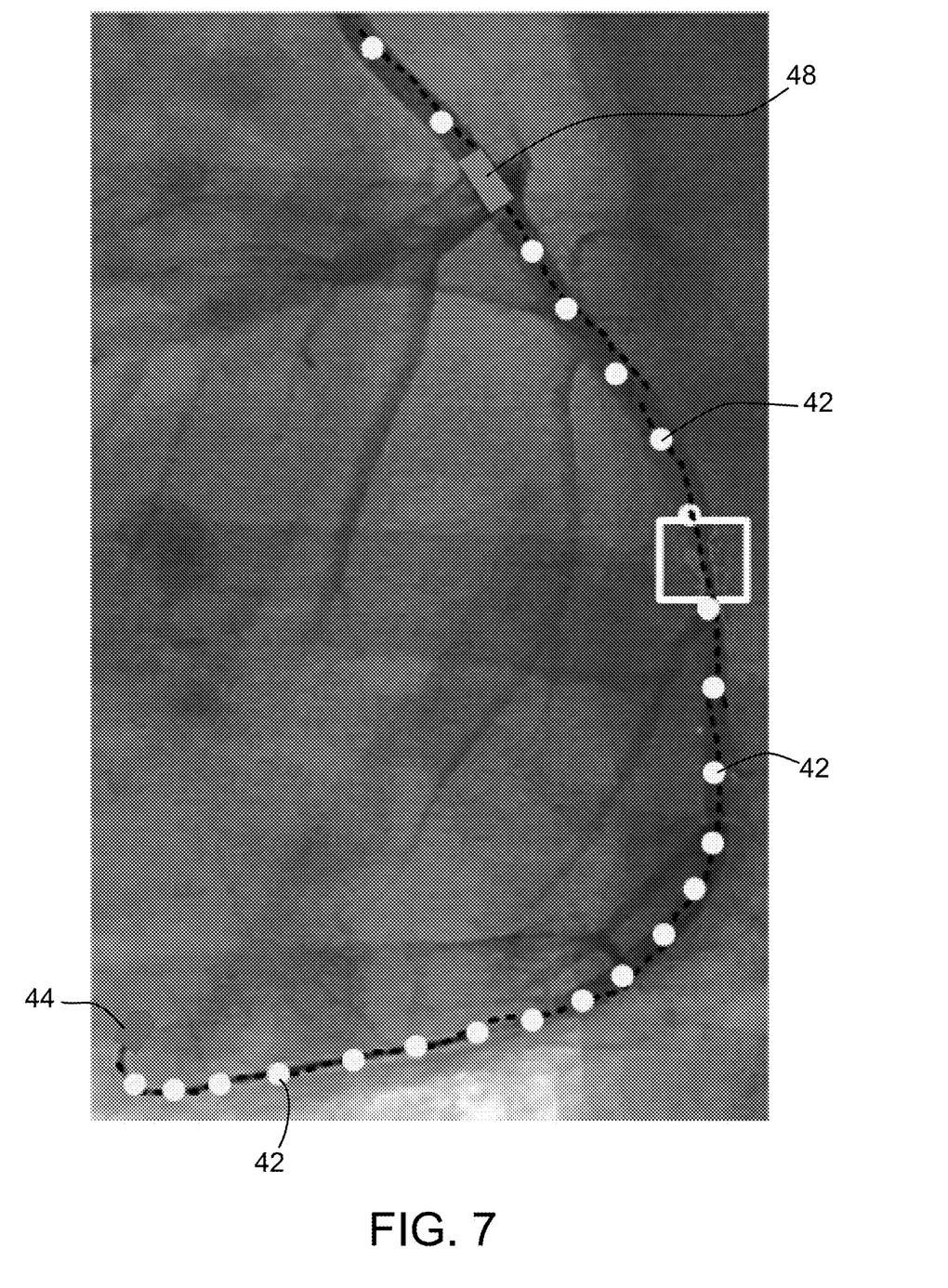
FIG. 7 is a photograph from a display similar to FIG. 6 but further including and showing a computed position of a catheter tip.
Figure 8:
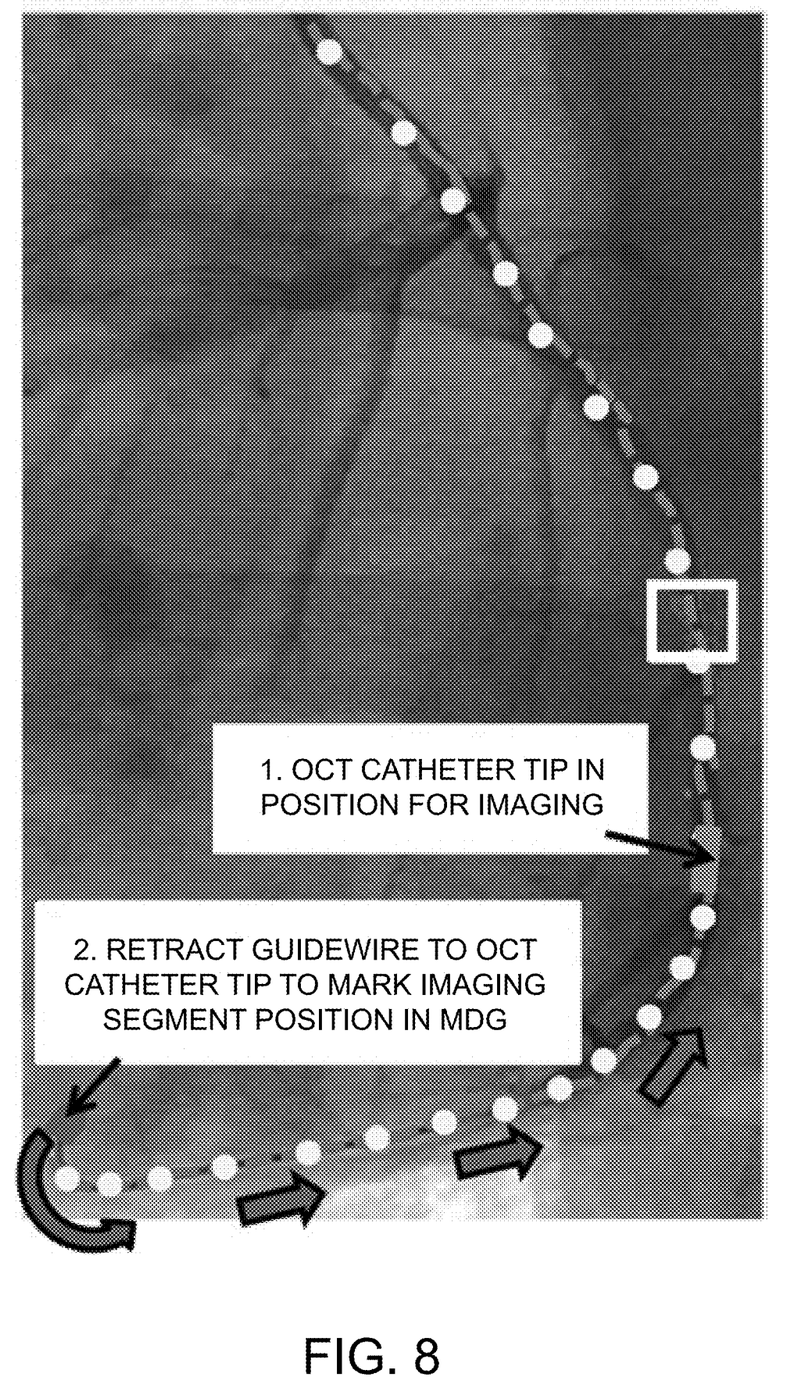
FIG. 8 is a photograph from a display showing a catheter tip in the desired position for imaging.
Figure 8A:
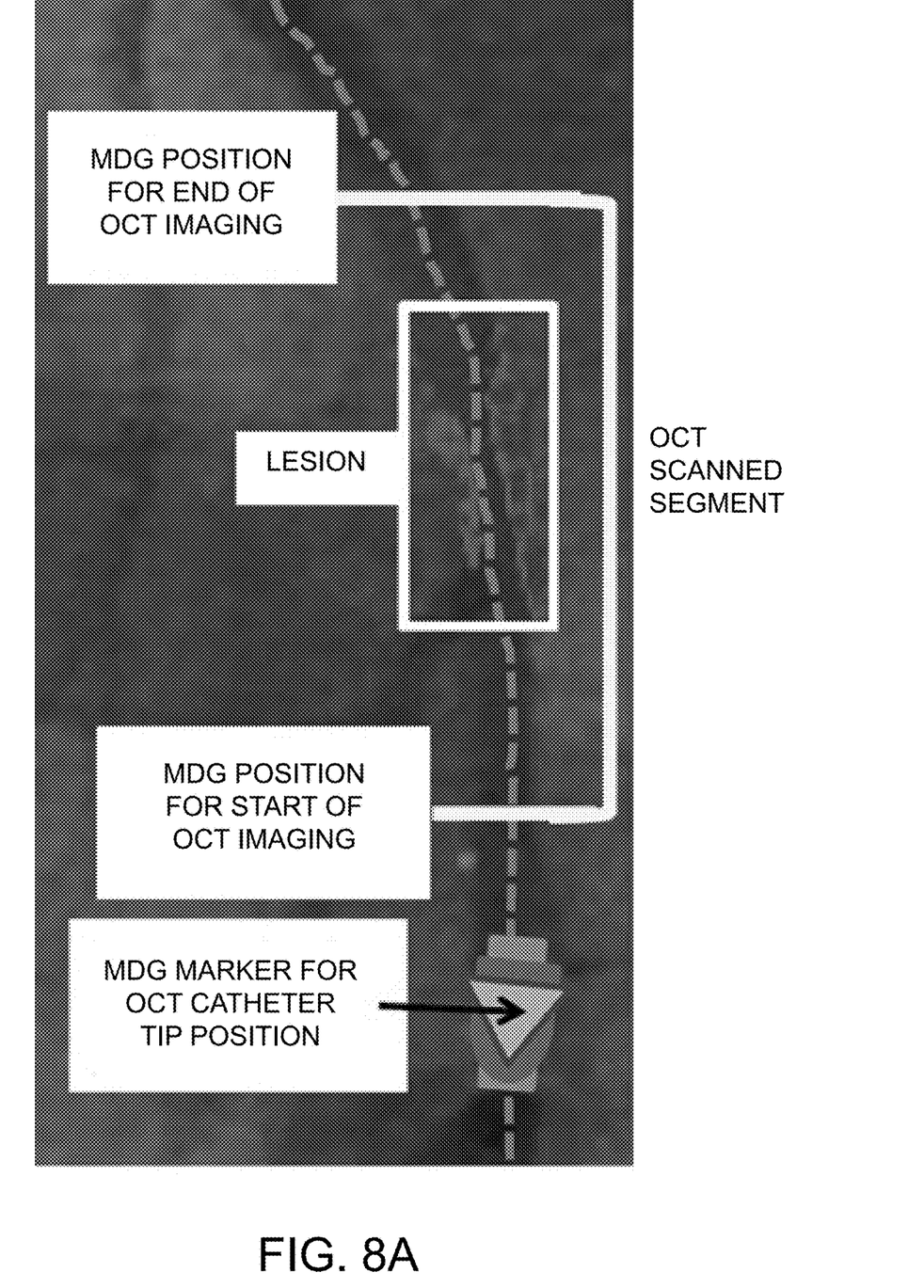
FIG. 8A is a photograph from a display similar to FIG. 8 and further showing an optical coherence tomography scanned segment.

In this embodiment, the vessel profile creation and spatial location is completed as described herein using the guidewire managing apparatus in combination with the sensor enabled guidewire and medical positioning system (See description above and FIGS. 5 and 6). A near-zero fluoroscopy OCT scan of the targeted lesion is done using a combination of the guidewire managing assembly described above (the OCT catheter is calibrated and measured using the guidewire managing assembly to assist in navigation) and the vessel profile produced under the first step (See FIG. 7, wherein box 48 represents the OCT catheter tip position computed using the guidewire managing assembly and medical positioning system as described above). Once this vessel profile is created, the operator can bring the OCT catheter tip distally to the vessel lesion, in position for intravascular OCT imaging. Prior to the OCT scan initiation, the sensor enabled guidewire may optionally be retracted to align its tip with the OCT catheter tip using the guidewire managing assembly described hereinabove (See FIG. 8). Upon the confirmation of the desired alignment of the OCT catheter tip and the sensor enabled guidewire tip by the guidewire managing assembly, the OCT catheter tip position and orientation is saved in the medical positioning system and in the advanced visualizer and used with the desired pullback length, to display on the vessel profile on the cine-loop in the beginning and end of the OCT scan (See FIG. 8A). The operator may then prepare for the OCT scan. While keeping the OCT catheter position fixed, the sensor enabled guidewire is returned to its original position before initiating the OCT scan. Upon verification and validation of the OCT scan, the PCI planning and optimization procedure is initiated by the operator. All relevant information (i.e., target zone for the balloon, thrombus, vessel dissection, calcified zone, etc.) is translated to the OCT 3D geometry ready to be imported into the advanced visualizer.

Figure 9:
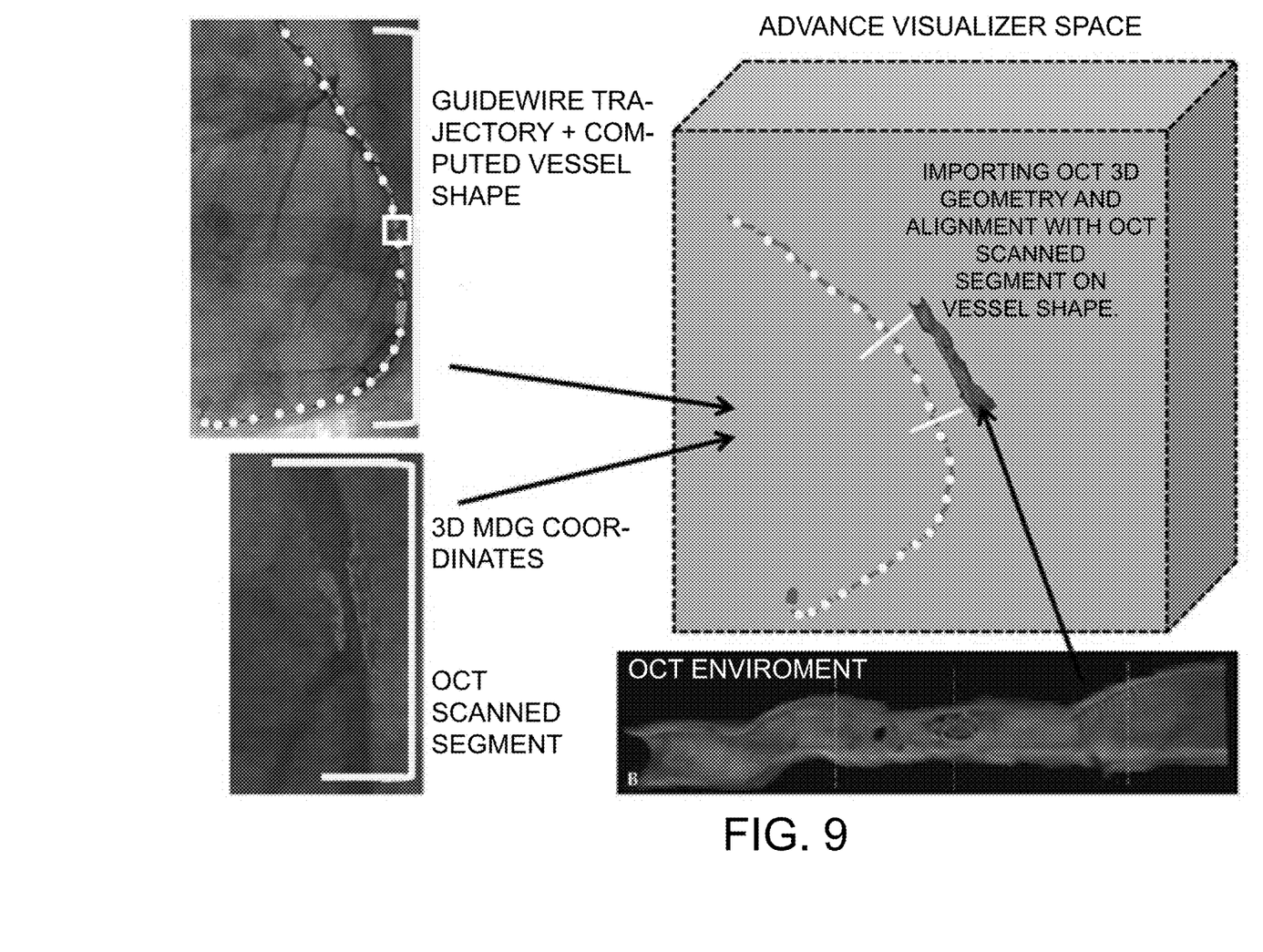
FIG. 9 includes photographs from a display illustrating the elements imported into an advance visualizer to allow for correctly aligned navigation in optical coherence tomography geometry.

Once the OCT scan is complete as noted above, the vessel profile (as determined by the medical positioning system) with OCT scan landmarks are imported first in the advanced visualizer environment followed by the OCT 3D geometry. A manual alignment process is then completed in the advanced visualizer software between the OCT 3D geometry and the beginning and end landmarks of the OCT scan on the vessel profile (see FIG. 9 illustrating the elements imported into the advanced visualizer to allow correctly aligned navigation in the OCT 3D geometry). Finally, the balloon catheter may be introduced over the sensor enabled guidewire and advanced toward the targeted vessel. When the target vessel is reached, using the guidewire managing assembly and medical positioning system as described herein, the position of the balloon catheter tip is plotted in the advanced visualizer thus allowing the operator to locate the tip of the balloon catheter versus the targeted lesion (then displayed in the high resolution 3D OCT geometry). The operator is able to guide the balloon catheter distally to the targeted lesion and reach the optimal position for balloon expansion. Also, using the catheter tip position and the balloon catheter specification sheet, the operator could display not only the catheter tip but the balloon position as well in the advanced visualizer. The operator may then expand the balloon.

As will be recognized by one skilled in the art based on the disclosure herein, the methods above-described could be expanded to cases involving multiple lesions where, after establishing the vascular network profile bearing the targeted lesions, the operator would import multiple 3D OCT geometries. The operator would then manually align each geometry at the correct location in the coronary arterial tree before localizing the catheter in the vascular network and bring on each site a balloon catheter with a stent to be deployed.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A guidewire managing assembly for determining the location of a medical device in a subject during a procedure, the assembly comprising:
   a guidewire including at least one medical positioning sensor, the guidewire extending from a tip to a proximal end;
   an entry port for the guidewire including at least one medical positioning sensor;
   a measurement device comprising a measurement wheel and a wheel locking mechanism operable to selectively prevent rotation of the measurement wheel, wherein the measurement wheel is configured to measure i) a first length of the guidewire when the tip of the guidewire is aligned with a distal end of a catheter shaft and ii) a second length of the guidewire when the proximal end of the guidewire is aligned with the measurement wheel;
   a circuit operable to i) record the first and second lengths measured by the measurement wheel and ii) calculate an entire length of the guidewire by summing the first and second lengths; and
   a transmitter operable to transmit the calculated entire length of the guidewire to a separate component.

2. The assembly of claim 1 wherein the assembly is coupleable to a catheter handle.

3. The assembly of claim 2 wherein the catheter handle is coupled to a luer-lock port.

4. The assembly of claim 3 further comprising a luer-lock tip that engages the luer-lock port.

5. The assembly of claim 4 further including the catheter shaft.

6. The assembly of claim 1 further including a display.

7. The assembly of claim 1 wherein the transmitter comprises a wireless antenna.

8. The assembly of claim 1, wherein the separate component is a medical positioning system.

9. The assembly of claim 1, wherein the wheel locking mechanism is operable to de-activate and permit rotation of the measurement wheel when the tip of the guidewire is aligned with the measurement wheel.

* * * * *